US010925627B1

(12) United States Patent
Kim et al.

(10) Patent No.: US 10,925,627 B1
(45) Date of Patent: Feb. 23, 2021

(54) CORDLESS ULTRASONIC SURGERY INSTRUMENT CAPABLE OF ENERGY HARVESTING

(71) Applicant: METABIOMED CO., LTD., Cheongju-si (KR)

(72) Inventors: Young June Kim, Cheongju-si (KR); Sang Min Lee, Cheongju-si (KR); Deog Nam Park, Cheongju-si (KR); Seung Hwan Kim, Cheongju-si (KR); Sun Ho Choe, Cheongju-si (KR)

(*) Notice: Subject to any disclaimer, the term of this patent is extended or adjusted under 35 U.S.C. 154(b) by 0 days.

(21) Appl. No.: 16/988,598

(22) Filed: Aug. 8, 2020

(30) Foreign Application Priority Data

Dec. 21, 2019 (KR) .................. 10-2019-0172559

(51) Int. Cl.
*A61B 17/32* (2006.01)
*A61B 17/04* (2006.01)
*A61B 17/00* (2006.01)

(52) U.S. Cl.
CPC .. *A61B 17/320068* (2013.01); *A61B 17/0469* (2013.01); *A61B 2017/00402* (2013.01);
(Continued)

(58) Field of Classification Search
CPC ........... A61B 2017/00398; A61B 2017/00734; A61B 2017/00017; A61B 18/1445; A61B 2018/0063; A61B 17/320092; A61B 17/320068; A61B 18/1206; A61B 2018/00994; A61B 17/29; A61B 2018/00589; A61B 2018/00607; A61B 2018/00595; A61B 2017/320069;
(Continued)

(56) References Cited

U.S. PATENT DOCUMENTS

2012/0045976 A1    2/2012   Roser et al.
2017/0252088 A1*   9/2017   Honda ................... A61B 17/32

FOREIGN PATENT DOCUMENTS

JP      2008-537901    10/2008
JP         6109448     4/2017
(Continued)

OTHER PUBLICATIONS

English Specification of 6109448.
(Continued)

*Primary Examiner* — Katherine M Shi
(74) *Attorney, Agent, or Firm* — Antonio Ha & U.S. Patent, LLC

(57) ABSTRACT

According to an embodiment, a cordless ultrasonic surgery instrument comprises an end effector directly contacting a tissue for incision or suture of the tissue, a handpiece including at least one or more piezoelectric elements to transfer vibration energy to the end effector, a hand instrument including a controller controlling an operation of the end effector and controlling to increase power from a power source device, a shaft assembly coupled with the end effector, rotated by receiving the vibration energy from the handpiece, converting part of vibration energy according to the vibration into electrical energy, and collecting the electrical energy, and a battery supplying power to the handpiece to allow the handpiece to transfer the vibration energy to the end effector, the battery charged with the electrical energy transmitted from the shaft assembly.

4 Claims, 5 Drawing Sheets

(52) U.S. Cl.
CPC .............. *A61B 2017/00734* (2013.01); *A61B 2017/320082* (2017.08)

(58) Field of Classification Search
CPC ........... A61B 2017/0046; A61B 2017/320088; A61B 17/0469; A61B 2017/00402; A61B 2017/320082
See application file for complete search history.

(56) References Cited

FOREIGN PATENT DOCUMENTS

| KR | 10-2009-0009150 | 1/2009 |
|----|-----------------|--------|
| KR | 10-2012-0093273 | 8/2012 |
| KR | 10-2015-0003292 | 1/2015 |
| KR | 10-2015-0008153 | 1/2015 |
| KR | 10-4744435      | 6/2017 |

OTHER PUBLICATIONS

English Specification of 10-2009-0009150.
English Specification of 2008-537901.
English Specification of 10-1744435.
English Specification of 10-2015-0008153.
English Specification of 10-2015-0003292.
English Specification of 10-2012-0093273.

* cited by examiner

CORDLESS ULTRASONIC SURGERY INSTRUMENT CAPABLE OF ENERGY HARVESTING

CROSS-REFERENCE TO RELATED APPLICATIONS

This application is based on and claims priority under 35 U.S.C. 119 to Korean Patent Application No. 10-2019-0172559, filed on Dec. 21, 2019, in the Korean Intellectual Property Office, the disclosure of which is herein incorporated by reference in its entirety.

TECHNICAL FIELD

Embodiments of the disclosure relate to a cordless ultrasonic surgery instrument capable of energy harvesting or collection.

DESCRIPTION OF RELATED ART

The description of the Discussion of Related Art section merely provides information that may be relevant to embodiments of the disclosure but should not be appreciated as necessarily constituting the prior art.

Surgical scalpels have been conventionally used to cut or dissect an organ or tissue. However, there is a fear that the conventional scalpel may cause bleeding due to vascular damage and infection due to vascular damage. Furthermore, the conventional scalpel has the inconvenience of increasing the operation time by requiring a separate suture process.

To address these issues, surgical devices using energy have been developed. There are known surgical devices using energy, such as ultrasonic, radio frequency (RF), laser, or plasma energy.

Among them, an ultrasonic surgery instrument using ultrasonic energy is a piece of surgical equipment used in various surgical fields such as general surgery, orthopedics, ophthalmology, plastic surgery, urology, or neurosurgery, and performs functions, such as tissue incision, fragmentation, ablation, and suture.

The ultrasonic surgery instrument includes an end effector having a blade that vibrates at an ultrasonic frequency to cut and suture tissue. The ultrasonic surgery instrument converts electric power into ultrasonic vibration using a piezoelectric element, and the converted ultrasonic vibration is transmitted to the blade element along an acoustic waveguide. With the action of a trigger, the end effector grips or separates from the tissue, and the tissue is excised and sutured by the transmitted ultrasonic vibration.

According to power supply methods, ultrasonic surgery instruments are divided into corded ultrasonic surgery instruments that are continuously supplied power through a wire and cordless ultrasonic surgery instruments that receive power from a precharged battery. Since the wireless ultrasonic surgery instrument is supplied with power from a precharged battery, the operating time of the cordless ultrasonic surgery instrument varies depending on the capacity and charged state of the battery. However, for increased battery capacity, the cordless ultrasonic surgery instrument has a bigger and heavier battery and, thus, the user of the cordless ultrasonic surgery instrument may feel uncomfortable.

Since the cordless ultrasonic surgery instrument is a surgical tool used in the surgical process, battery replacement in the surgical process might jeopardize the patient or interfere with the success of the surgery. Therefore, a need exists for a method capable of increasing the operating time of a cordless ultrasonic surgery instrument by using part of the energy generated while driving the cordless ultrasonic surgery instrument to charge the battery while supplying sufficient power to the cordless ultrasonic surgery instrument.

SUMMARY

According to an embodiment, there is provided a cordless ultrasonic surgery instrument capable of collecting part of the energy, used to drive the cordless ultrasonic surgery instrument, as electrical energy to increase the operating time of the cordless ultrasonic surgery instrument.

According to an embodiment, a cordless ultrasonic surgery instrument comprises an end effector directly contacting a tissue for incision or suture of the tissue, a handpiece including at least one or more piezoelectric elements to transfer vibration energy to the end effector, a hand instrument including a controller controlling an operation of the end effector and controlling to increase power from a power source device, a shaft assembly coupled with the end effector, rotated by receiving the vibration energy from the handpiece, converting part of vibration energy according to the vibration into electrical energy, and collecting the electrical energy, and a battery supplying power to the handpiece to allow the handpiece to transfer the vibration energy to the end effector, the battery charged with the electrical energy transmitted from the shaft assembly. The shaft assembly may include a propagation rod rotated by the vibration energy received from the handpiece, a charging patch converting part of the vibration energy generated according to movement of the propagation rod into electrical energy, and collecting the electrical energy, and a pressurizing ring positioned between the charging patch and the propagation rod and pressurizing the charging patch to prompt generation of the electrical energy.

According to an embodiment, a cordless ultrasonic surgery instrument comprises an end effector directly contacting a tissue for incision or suture of the tissue, a handpiece including at least one or more piezoelectric elements to transfer vibration energy to the end effector, a hand instrument including a controller controlling an operation of the end effector and controlling to increase power from a power source device, a shaft assembly coupled with the end effector, rotated by receiving the vibration energy from the handpiece, converting part of vibration energy according to the vibration into electrical energy, and collecting the electrical energy, and a battery supplying power to the handpiece to allow the handpiece to transfer the vibration energy to the end effector, the battery charged with the electrical energy transmitted from the shaft assembly. The shaft assembly includes a propagation rod rotated by the vibration energy received from the handpiece, a charging patch converting part of the vibration energy generated according to movement of the propagation rod into electrical energy, and collecting the electrical energy, and an embossed pressurizing ring positioned between the charging patch and the propagation rod, the embossed pressurizing ring including a row of protrusions forming a group of grooves to pressurize the charging patch.

The charging patch is electrically connected directly with the battery to directly charge the battery with the collected electrical energy.

According to the embodiments of the disclosure, part of the energy used to drive the cordless ultrasonic surgery instrument may be converted into and collected as electrical energy, thereby increasing the operating time of the cordless ultrasonic surgery instrument.

BRIEF DESCRIPTION OF THE DRAWINGS

A more complete appreciation of the disclosure and many of the attendant aspects thereof will be readily obtained as the same becomes better understood by reference to the following detailed description when considered in connection with the accompanying drawings, wherein.

DETAILED DESCRIPTION

Various changes may be made to the disclosure, and the disclosure may come with a diversity of embodiments. Some embodiments of the disclosure are shown and described in connection with the drawings. However, it should be appreciated that the disclosure is not limited to the embodiments, and all changes and/or equivalents or replacements thereto also belong to the scope of the disclosure. Similar reference denotations are used to refer to similar elements throughout the drawings.

The terms "first" and "second" may be used to describe various components, but the components should not be limited by the terms. The terms are used to distinguish one component from another. For example, a first component may be denoted a second component, and vice versa without departing from the scope of the disclosure. The term "and/or" may denote a combination(s) of a plurality of related items as listed or any of the items.

It will be understood that when an element or layer is referred to as being "on," "connected to," "coupled to," or "adjacent to" another element or layer, it can be directly on, connected, coupled, or adjacent to the other element or layer, or intervening elements or layers may be present. In contrast, when a component is "directly connected to" or "directly coupled to" another component, no other intervening components may intervene therebetween.

The terms as used herein are provided merely to describe some embodiments thereof, but not to limit the disclosure. As used herein, the singular forms "a," "an," and "the" are intended to include the plural forms as well, unless the context clearly indicates otherwise. As used herein, the term "comprise," "include," or "have" should be appreciated not to preclude the presence or addability of features, numbers, steps, operations, components, parts, or combinations thereof as set forth herein.

Unless otherwise defined, all terms including technical and scientific terms used herein have the same meaning as commonly understood by one of ordinary skill in the art to which the embodiments of the disclosure belong.

It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The components, processes, steps, or methods according to embodiments of the disclosure may be shared as long as they do not technically conflict with each other.

Figure 1:
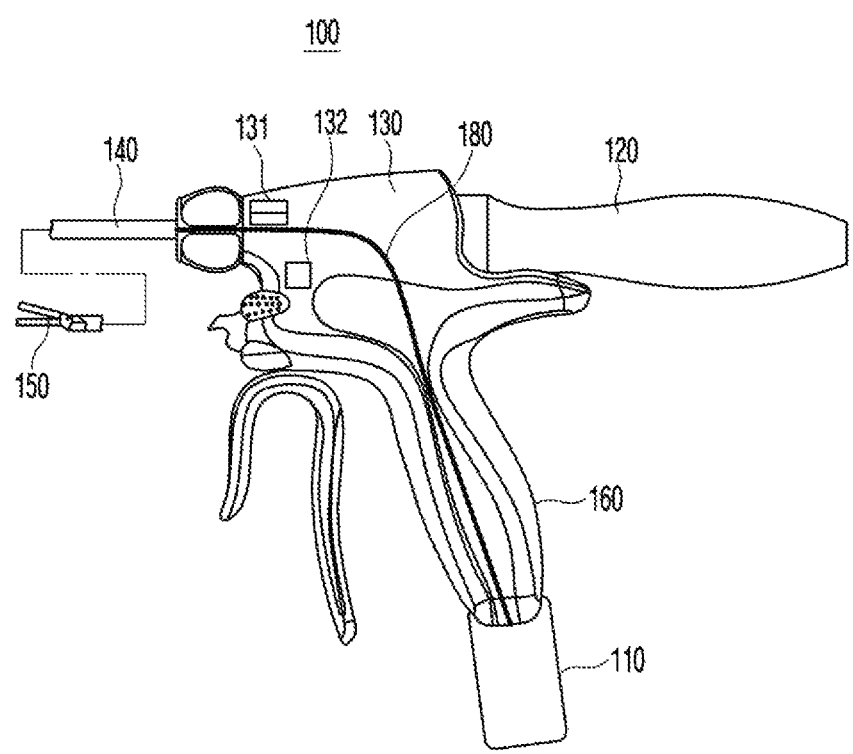
FIG. 1 is a cordless ultrasonic surgery instrument according to an embodiment.

FIG. 1 is a cordless ultrasonic surgery instrument according to an embodiment.

Referring to FIG. 1, according to an embodiment, a cordless ultrasonic surgery instrument 100 includes a battery 110, a handpiece 120, a hand instrument 130, a shaft assembly 140, an end effector 150, a handle assembly 160, and an adapter 170.

The battery 110 supplies power to the handpiece 120 to vibrate.

The battery 110 may be supplied and charged with energy collected by the shaft assembly 140 or may be charged by an external power source. The battery 110 may be configured to be detachable in the handle assembly 160 and includes a power supply ground unit and a charging ground unit. The power supply ground unit may be implemented as a circuit for performing the functions or operations of the power supply ground unit. The charging ground unit may be implemented as a circuit for performing the functions or operations of the charging ground unit. The power supplying ground unit is electrically connected with the handpiece 120 to allow power to be supplied to the handpiece 120. The charging ground unit is supplied and charged with electric energy gathered by the shaft assembly 140. The battery 110 is electrically connected directly with a connecting circuit 180 and receives the electric energy, collected by the shaft assembly 140, via the connecting circuit 180.

The handpiece 120 may receive power from the battery 110 to generate ultrasonic vibration energy and transfers ultrasonic vibration energy to the shaft assembly 140.

The handpiece 120 receives power from a power source, e.g., the battery 110, and generates vibration energy. The handpiece 120 includes a piezoelectric element that converts electrical energy into vibration energy or converts vibration energy into electrical energy. The piezoelectric element receives power from the battery 110 and converts the power into vibration energy.

The handpiece 120 transfers the generated ultrasonic vibration (or vibration energy) to the shaft assembly 140. The handpiece 120 is coupled to the hand instrument 130 and is thereby connected with the shaft assembly 140. The handpiece 120 transfers the generated vibration energy to the shaft assembly 140 so that the generated vibration energy may be transfer up to the end effector 150.

The hand instrument 130 fixes or fastens the handpiece 120 and shaft assembly 140 and controls each component, or its operation, of the cordless ultrasonic surgery instrument 100.

The hand instrument 130 fixes or fastens the handpiece 120 and the shaft assembly 140. The hand instrument 130 includes an insertion hole for the handpiece 120 and the shaft assembly 140, and the insertion hole of the hand instrument 130 allows the handpiece 120 and the shaft assembly 140 to be inserted into the inside of the hand instrument 130. The hand instrument 130 fixes or fastens the handpiece 120 and shaft assembly 140 inserted thereto and transfers the vibration energy generated by the handpiece 120 to the shaft assembly 140. The vibration energy is transferred via the shaft assembly 140 up to the end effector 150.

The hand instrument 130 includes a controller 132 thereinside to control each component, or its operation, of the cordless ultrasonic surgery instrument 100. The hand instrument 130 includes an input unit 131 for receiving inputs, e.g., a method for operating the end effector 150, from the user, and the controller 132 controls each component, or its operation, of the cordless ultrasonic surgery instrument 100 according to the user's input. The input unit 131 may be a circuit implemented to perform the functions or operations of the input unit. For example, in a case where the input unit 131 receives an input, for incising the tissue using the end effector 150, from the user, the controller 132 increases the power or output of the battery 110 to thereby increase the amount of the vibration energy generated by the handpiece 120. When the battery 110 is not in the fully charged state, the controller 132 charges the battery 110 with the electrical energy obtained by the shaft assembly 140 from the vibration energy generated by the handpiece 120.

The shaft assembly 140 includes a tubular propagation rod and a charging patch. The tubular propagation rod and transfers the vibration energy, which is transferred from the hand instrument 130, to the end effector 150, and the charging patch converts the pressure energy, which is generated as the tubular propagation rod moves and hits, into electrical energy.

An end of the shaft assembly 140 is connected with the end effector 150, and the other end thereof is inserted to the insertion hole of the hand instrument 130 and is fastened. The shaft assembly 140 is fastened by the hand instrument 130 and receives vibration energy from the hand instrument 130 and transfers the received vibration energy to the end effector 150. At this time, the shaft assembly 140 may be rotated in the insertion hole of the hand instrument 130 and, as rotated, may control the direction of the end effector 150.

The shaft assembly 140 may collect part of the mechanical shock or impact energy, which is generated as the shaft assembly 140 is rotated while transferring the vibration energy to the end effector 150, as electrical energy and supply the electrical energy to the battery 110. The charging pad is included in the shaft assembly 140. Part of the impact energy applied to the charging pad while the shaft assembly 140 is rotated in the insertion hole of the hand instrument 130 may be collected as electrical energy. The shaft assembly 140 supplies the collected electrical energy to the battery 110 via the hand instrument 130.

The end effector 150 holds or grips the tissue and then cuts or sutures the tissue using the received vibration energy. The end effector 150 holds the tissue or moves away from the tissue according to the operation of the handle assembly 160. While holding the tissue, the end effector 150 cuts and sutures the tissue using the received vibration energy.

The handle assembly 160 allows the user to grip the cordless ultrasonic surgery instrument 100 and control the operation of the end effector 150. The handle assembly 160 includes a handle to allow the user to grip the cordless ultrasonic surgery instrument 100 and a trigger to control the holding or gripping operation of the end effector 150.

The adapter 170 connects the shaft assembly 140 with the hand instrument 130 and fastens an end of the shaft assembly 140 to the hand instrument 130 even when the shaft assembly 140 rotates. The adapter 170 is formed of a material capable of transferring the vibration energy from the handpiece 120 to the shaft assembly 140 and includes a circuit that may form a path along which the energy collected by the shaft assembly 140 is transferred to the battery 110.

The connecting circuit 180 may connect the battery 110 and the shaft assembly 140. When current is rendered to flow by the shaft assembly 140, the connecting circuit 180 transfers the current to the battery 110 so that the battery 110 may be charged with the electrical energy collected by the shaft assembly 140.

Figure 2:
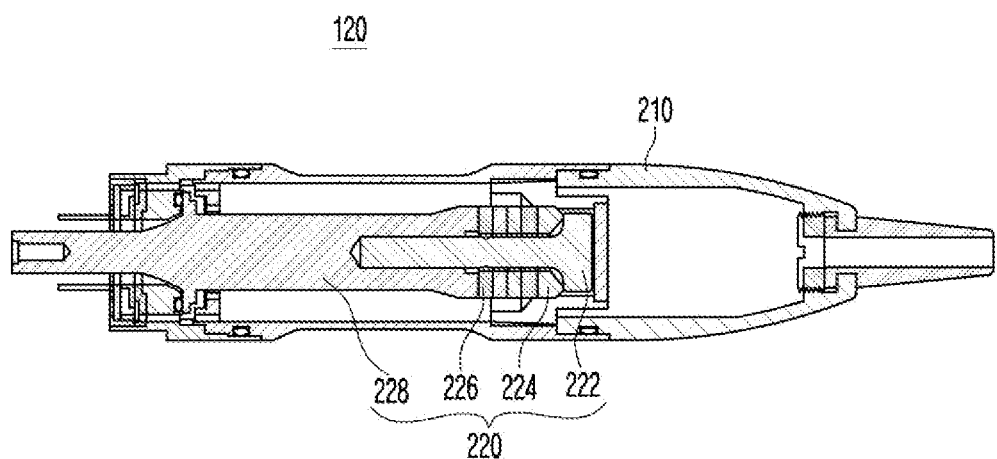
FIG. 2 is a view illustrating a configuration of a handpiece according to an embodiment.

FIG. 2 is a view illustrating a configuration of a handpiece according to an embodiment.

Referring to FIG. 2, according to an embodiment, the handpiece 120 includes a housing 210 and a vibrator 220.

The vibrator 220 is placed inside the housing 210 and receives power from a power source and thus vibrates.

The vibrator 220 includes a fastening element 222, a tail mass 224, a piezoelectric element 226, and a head horn 228.

As the fastening element 222 is coupled with the head horn 228 via the piezoelectric element 226, the piezoelectric element 226 is fastened between the fastening element 222 and the head horn 228 as shown in FIG. 2. As torque is exerted from the outside to the fastening element 222, the fastening element 222 and the head horn 228 may be coupled together. The fastening element 222 may be implemented as a bolt as an example, and an end of the head horn 228 may be threaded so that the fastening element 222 and the head horn 228 may be coupled together.

The torque acting on the fastening element 222 allows the fastening element 222 to apply a force to the piezoelectric element 226, the head horn 228 also applies the same magnitude of force to the piezoelectric element 226 as a reaction to the force exerted by the fastening element 222. The piezoelectric element 226 is fastened by the coupling between the fastening element 222 and the head horn 228.

The piezoelectric element 226 receives power from the battery 110 and generates vibration energy. The vibration energy generated by the piezoelectric element 226 is varied depending on the frequency provided to the piezoelectric element 226. The piezoelectric element 226 generates the largest vibrational energy at the natural frequency, and the piezoelectric element 226 may change its properties, such as natural frequency, by fastening torque by the fastening element 222.

Figure 3:
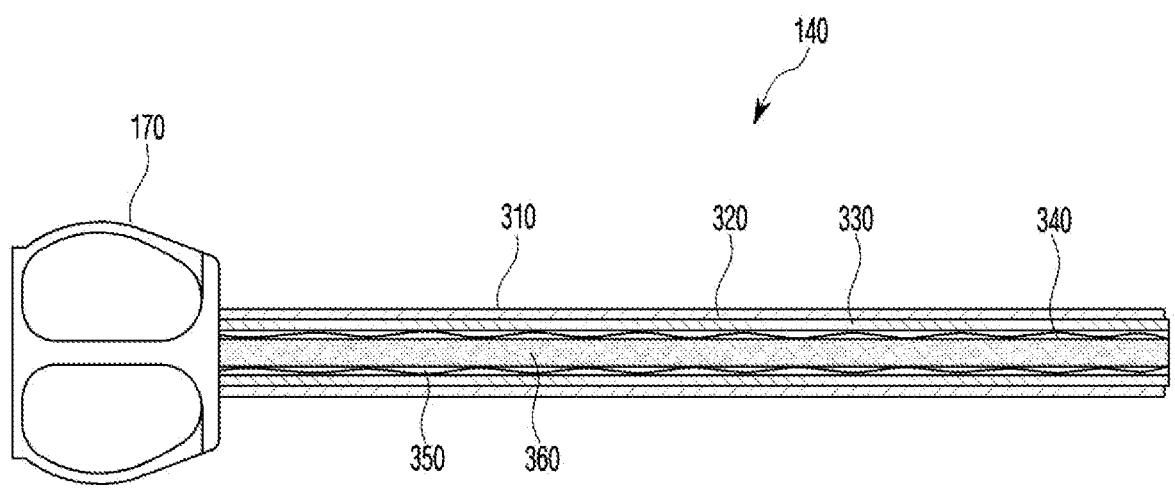
FIG. 3 is a view illustrating a configuration of a shaft assembly according to an embodiment.

FIG. 3 is a view illustrating a configuration of a shaft assembly according to an embodiment.

Referring to FIG. 3, according to an embodiment, the shaft assembly 140 includes a metal tube 310, an insulation member 320, a charging patch 330, a cavity 340, an impact transfer medium 350, and a propagation rod 360.

The metal tube 310 receives the insulation member 320, the charging patch 330, and the propagation rod 360 thereinside. The metal tube 310 has an end connected to the adapter 170 and another end connected to the end effector 150. The metal tube 310 may be formed of a metallic material and may thus transfer leakage current to the outside. Thus, the inside of the metal tube 310 is coated with the insulation member 320 to prevent the patient from electric shocks when the cordless ultrasonic surgery instrument 100 operates.

The insulation member 320 may be interposed between the metal tube 310 and the charging patch 330. The insulation member 320 may be formed of a material, e.g., silicone, to block an electrical flow to the outside.

The charging patch 330 converts the vibration energy from the propagation rod 360 into electrical energy. As the propagation rod 360 located inside the impact transfer medium 350 is vibrated, an impact is applied to the charging patch 330 while the impact transfer medium 350 is moved. The charging patch 330 converts the generated mechanical energy (impacts) into electrical energy.

The charging patch 330 may include a piezopolymer, such as of polyvinylidene fluoride (PVDF). When the impact transfer medium 350 applies an impact (thus pressure) to the charging patch 330, the charging patch 330 may generate a voltage with the pressure applied to the charging patch 330. The charging patch 330 may wrap the entire interior of the metal tube 310 and simultaneously collect electrical energy from a plurality of impact sites. The larger pressure is applied to the charging patch 330, the more electrical energy may be collected by the charging patch 330.

The charging patch 330 may transfer the collected electrical energy directly to the battery 110 via the connecting circuit 180. The charging patch 330 may be connected directly to the connecting circuit 180 via, e.g., a conducting wire, and be connected up to the battery 110 via the connecting circuit 180. Thus, the charging patch 330 transfers electrical energy to the battery 110 whenever electrical energy is generated from the charging patch 330. The current may flow to the connecting circuit 180 and up to the battery 110, allowing the battery 110 to be charged. The connecting circuit 180 is configured as a separate circuit from the circuit by which the battery 110 transfers power to the handpiece 120.

The cavity 340 is an empty space in the metal tube 310. The cavity 340 receives the impact transfer medium 350 and provides a path along which the impact transfer medium 350 moves.

The impact transfer medium 350 is a flowable material and is moved in the cavity 340 along the vibration direction of the propagation rod 360 which moves in the impact transfer medium 350. The larger vibration width (e.g., amplitude) the propagation rod 360 has, the larger impact is applied to the charging patch 330 by the impact transfer medium 350. In contrast, the smaller vibration width (e.g., amplitude) the propagation rod 360 has, the smaller impact is applied to the charging patch 330 by the impact transfer medium 350. Thus, the magnitude of pressure applied to the charging patch 330 by the impact transfer medium 350 is varied depending on the vibration energy of the propagation rod 360.

The propagation rod 360 may be shaped as a long, tubular stick or rod and may be formed of a material with a high elastic modulus that can flexibly react to impact.

The propagation rod 360 is rotated by the vibration energy received from the piezoelectric element 226, converts the rotational force or torque into kinetic energy, and transfers the kinetic energy up to the end effector 150 in a translational motion manner. The propagation rod 360 is moved in the impact transfer medium 350 while the cordless ultrasonic surgery instrument 100 operates and forms a waveform in the impact transfer medium 350.

Figure 4:
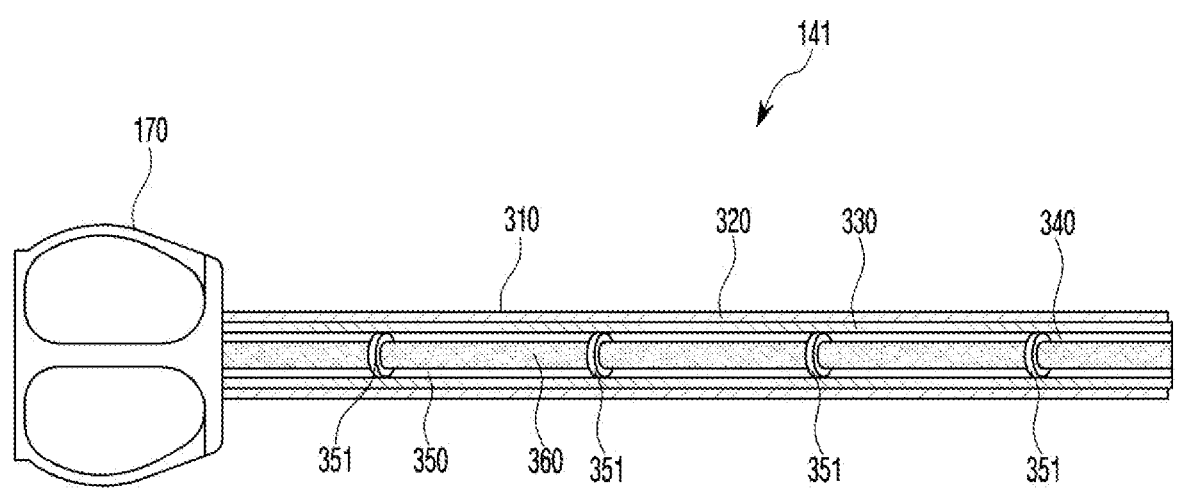
FIG. 4 is a view illustrating a configuration of a shaft assembly according to an embodiment.

FIG. 4 is a view illustrating a configuration of a shaft assembly 141 according to an embodiment.

Referring to FIG. 4, according to an embodiment, the shaft assembly 141 includes a metal tube 310, an insulation member 320, a charging patch 330, pressurizing rings 351, and a propagation rod 360.

According to an embodiment, the shaft assembly 140 141 has the pressurizing rings 351 attached to the propagation rod 360 so that the pressurizing rings 351 are moved when the propagation rod 360 is moved.

The pressurizing rings 351 are fitted over the propagation rod 360 and attached onto the propagation rod 360. Thus, the site where pressure is applied to the charging patch 330 is varied depending on the moving position of the propagation rod 360. The pressurizing rings 351 may be formed of a durable material which is not easily worn by friction and may be formed of a material having a low coefficient of friction so as not to interfere with the movement of the propagation rod 360 due to friction with the charging patch 330. For example, the pressurizing ring 351 may be formed of silicone.

While moving along the propagation rod 360, the pressurizing rings 351 may vary the sites where pressure is applied to the charging patch 330, so that a potential change occurs according to piezoelectricity. The charging patch 330 may collect the potential change according to piezoelectricity as electrical energy and transfer the electrical energy to the battery 110.

Figure 5:
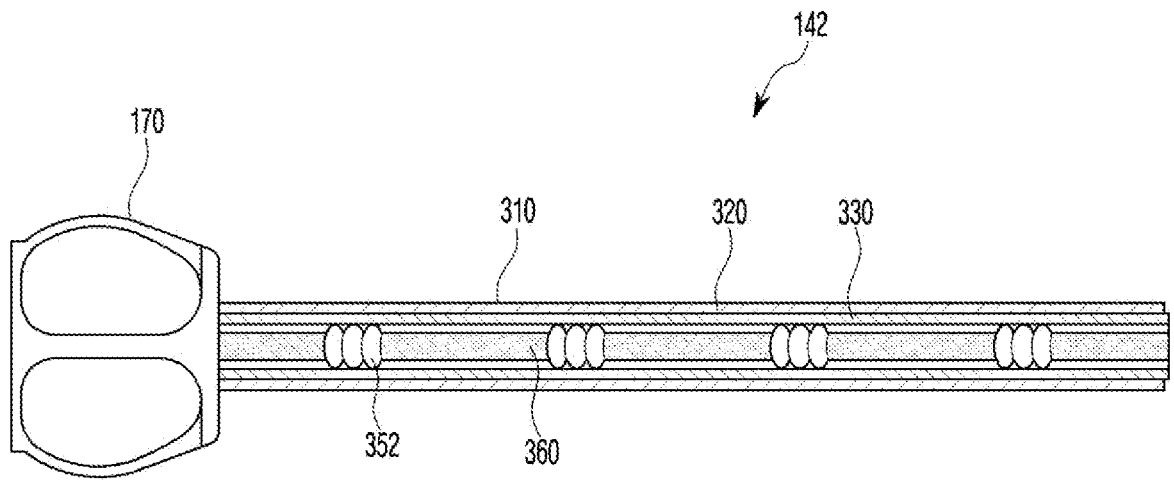
FIG. 5 is a view illustrating a configuration of a shaft assembly according to an embodiment.

FIG. 5 is a view illustrating a configuration of a shaft assembly according to an embodiment.

Referring to FIG. 5, according to an embodiment, the shaft assembly 142 includes a metal tube 310, an insulation member 320, a charging patch 330, embossed pressurizing rings 352, and a propagation rod 360.

According to an embodiment, the shaft assembly 140 142 has the embossed pressurizing rings 352 fitted over the propagation rod 360 so that the embossed pressurizing rings 352 are moved when the propagation rod 360 is moved.

Each of the embossed pressurizing rings 352 includes a row of protrusions forming a group of grooves. The row of protrusions of the embossed pressurizing ring 352 protrude to the charging patch 330. The embossed pressurizing ring 352 has a group of grooves so that only the protrusions of the embossed pressurizing ring 352 contact and pressurize the charging patch 330 unlike the pressurizing ring 351. Thus, as compared with the pressurizing rings 351, the embossed pressurizing rings 352 may reduce loss of vibration energy of the propagation rod 360 due to friction with the charging patch 330.

Figure 6:
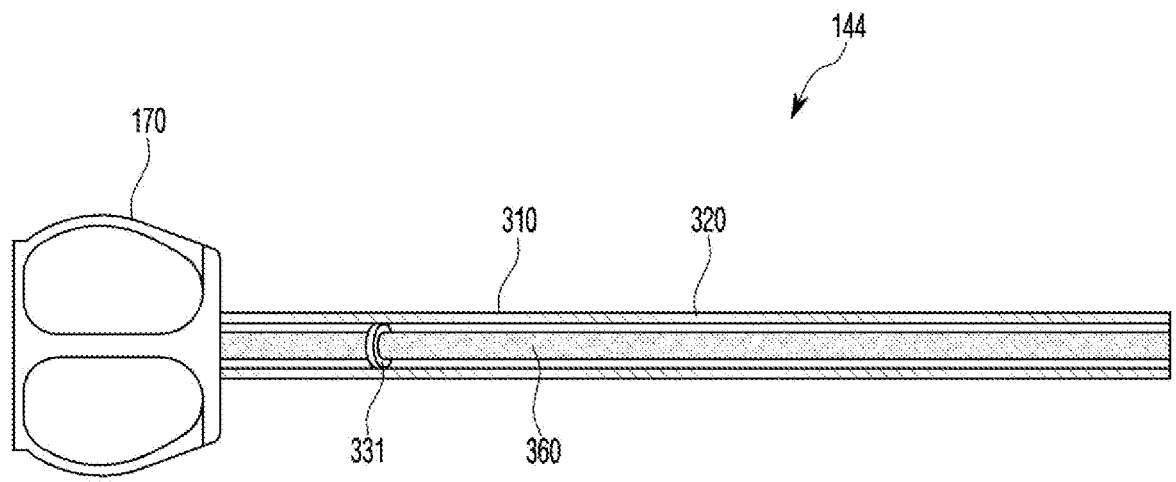
FIG. 6 is a view illustrating a configuration of a shaft assembly according to an embodiment.

FIG. 6 is a view illustrating a configuration of a shaft assembly according to an embodiment.

Referring to FIG. 6, according to an embodiment, the shaft assembly 144 includes a metal tube 310, an insulation member 320, a charging patch 331, and a propagation rod 360.

Referring to FIG. 6, according to an embodiment, the shaft assembly 144 includes the charging patch 331 positioned on the propagation rod 360. Thus, the charging patch 331 moves along with the propagation rod 360 along the moving path of the propagation rod 360. As the propagation rod 360 vibrates, the site where the charging patch 331 contacts the insulation member 320 is varied. Thus, the charging patch 331 may collect the piezoelectric energy generated the moment it touches on and off the insulation member 320 and charge the battery 110 with the piezoelectric energy.

Figure 7:
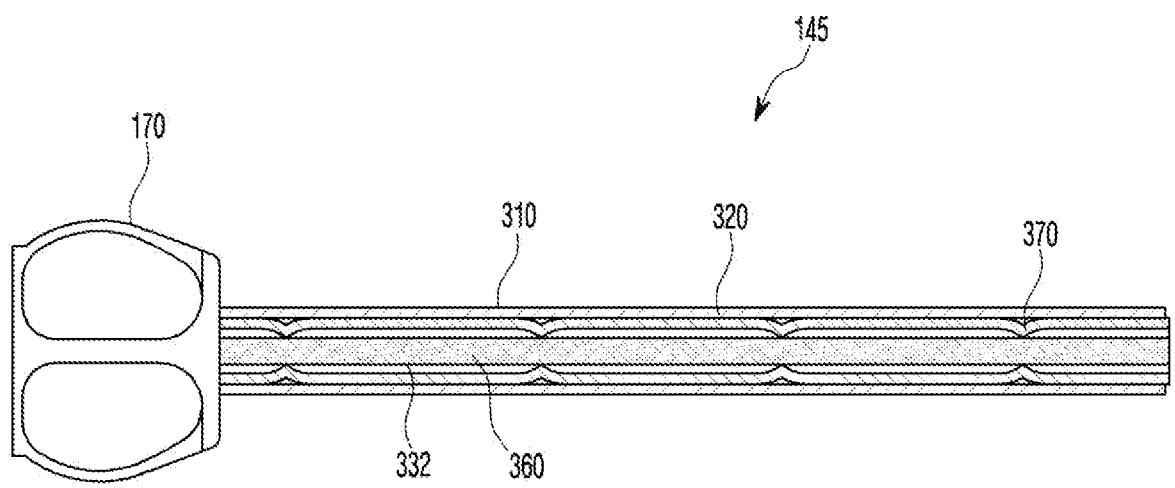
FIG. 7 is a view illustrating a configuration of a shaft assembly according to an embodiment.

FIG. 7 is a view illustrating a configuration of a shaft assembly according to an embodiment.

Referring to FIG. 7, according to an embodiment, the shaft assembly 145 includes a metal tube 310, an insulation member 320, a charging patch 332, a propagation rod 360, and pressurizing protrusions 370.

The pressurizing protrusions 370 may be formed on the insulation member 320 and be projected to the propagation rod 360. The plurality of pressurizing protrusions 370 pressurize the charging patch 332 to allow the charging patch 332 to produce a piezoelectric effect.

The charging patch 332 may be formed to wrap around the propagation rod 360. As the propagation rod 360 moves, the sites where the charging patch 332 contacts the pressurizing protrusions 370 may be varied, and the charging patch 332 may collect the piezoelectric energy generated the moment the charging patch 332 touches on and off the pressurizing protrusions 370 and charge the battery 110 with the piezoelectric energy.

The above-described embodiments are merely examples, and it will be appreciated by one of ordinary skill in the art various changes may be made thereto without departing from the scope of the disclosure. Accordingly, the embodiments set forth herein are provided for illustrative purposes, but not to limit the scope of the disclosure, and should be appreciated that the scope of the disclosure is not limited by the embodiments. The scope of the disclosure should be construed by the following claims, and all technical spirits within equivalents thereof should be interpreted to belong to the scope of the disclosure.

What is claimed is:

1. A cordless ultrasonic surgery instrument, comprising:
an end effector configured to directly contact a tissue for incision or suture of the tissue;
a handpiece including at least one or more piezoelectric elements to transfer vibration energy to the end effector;
a hand instrument including a controller controlling an operation of the end effector and controlling to increase power from a power source device;
a shaft assembly coupled with the end effector, rotated by receiving the vibration energy from the handpiece, converting part of vibration energy according to the vibration into electrical energy, and collecting the electrical energy; and
a battery supplying power to the handpiece to allow the handpiece to transfer the vibration energy to the end effector, the battery charged with the electrical energy transmitted from the shaft assembly, wherein
the shaft assembly includes a propagation rod rotated by the vibration energy received from the handpiece, a charging patch converting part of the vibration energy generated according to movement of the propagation rod into electrical energy, and collecting the electrical energy, and a pressurizing ring positioned between the charging patch and the propagation rod and pressurizing the charging patch to prompt generation of the electrical energy.

2. A cordless ultrasonic surgery instrument, comprising:
an end effector configured to directly contact a tissue for incision or suture of the tissue;
a handpiece including at least one or more piezoelectric elements to transfer vibration energy to the end effector;
a hand instrument including a controller controlling an operation of the end effector and controlling to increase power from a power source device;
a shaft assembly coupled with the end effector, rotated by receiving the vibration energy from the handpiece, converting part of vibration energy according to the vibration into electrical energy, and collecting the electrical energy; and
a battery supplying power to the handpiece to allow the handpiece to transfer the vibration energy to the end effector, the battery charged with the electrical energy transmitted from the shaft assembly, wherein
the shaft assembly includes a propagation rod rotated by the vibration energy received from the handpiece, a charging patch converting part of the vibration energy generated according to movement of the propagation rod into electrical energy, and collecting the electrical energy, and an embossed pressurizing ring positioned between the charging patch and the propagation rod, the embossed pressurizing ring including a row of protrusions forming a group of grooves to pressurize the charging patch.

3. The cordless ultrasonic surgery instrument of claim 1, wherein the charging patch is electrically connected directly with the battery to directly charge the battery with the collected electrical energy.

4. The cordless ultrasonic surgery instrument of claim 2, wherein the charging patch is electrically connected directly with the battery to directly charge the battery with the collected electrical energy.

* * * * *